(12) United States Patent
Shimura

(10) Patent No.: US 6,546,068 B1
(45) Date of Patent: Apr. 8, 2003

(54) IMAGE DATA ACQUISITION METHOD AND IMAGE DATA ACQUISITION DEVICE

(75) Inventor: Kazuo Shimura, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/487,724

(22) Filed: Jan. 19, 2000

(30) Foreign Application Priority Data

Jan. 19, 1999 (JP) .......................................... 11-010514

(51) Int. Cl.$^7$ ................................................ A61B 6/00
(52) U.S. Cl. ...................... 378/19; 378/98.8; 378/98.12
(58) Field of Search ................ 378/19, 4, 11, 378/14, 98.8, 98.12

(56) References Cited

U.S. PATENT DOCUMENTS

| | | | | |
|---|---|---|---|---|
| 5,319,693 A | * | 6/1994 | Eberhard et al. | 378/19 |
| 5,432,834 A | * | 7/1995 | Gershman | 378/196 |
| 5,802,138 A | * | 9/1998 | Glasser et al. | 378/98.8 |
| 5,848,114 A | | 12/1998 | Kawai et al. | 378/4 |

OTHER PUBLICATIONS

Cone–Beam CT—Present Status and Future Prospects, Image Information (M), pp. 122–127, Jan. 1988.
Practical cone–beam algorithm, L.A. Feldkamp, L.C. Davis, J.W. Kress, J. Opt. Soc. Am. A/vol. 1, No. 6, Jun. 1984.
Handbook of Image Analysis, Tokyo Univ. Publication., pp. 356–371 No date.

* cited by examiner

*Primary Examiner*—Drew A. Dunn
*Assistant Examiner*—Jurie Yun
(74) *Attorney, Agent, or Firm*—Sughrue Mion, PLLC

(57) ABSTRACT

A mover 13 moves and disposes a radiation detector 12 in a photographing position P1, and projected image data D21 is acquired for each of the directions of projection at this time. By use of the mover 13, the radiation detector 12 is moved to a photographing position P2, P3, and projected image data D22, D23 is acquired in each of the photographing positions as is the case with the photographing position P1. A projected image data synthesizer 31 in the image processor section 30 synthesizes the projected image data D21, D22, and D23 to generate synthesized projected image data D20, which is the projected image data for the entire detection region.

7 Claims, 4 Drawing Sheets

PHOTOGRAPHING POSITION P1

PHOTOGRAPHING POSITION P2

PHOTOGRAPHING POSITION P3

FIG.3A  FIG.3B  FIG.3C

PHOTOGRAPHING POSITION P1

PHOTOGRAPHING POSITION P2

PHOTOGRAPHING POSITION P3

PHOTOGRAPHING POSITION
P1←12a
P3←12b

FIG. 8C

PHOTOGRAPHING POSITION
P2←12a
P4←12b

FIG. 9A

PHOTOGRAPHING POSITION
P1←12a
P2←12b

FIG. 9B

PHOTOGRAPHING POSITION
P3←12a
P4←12b

IMAGE DATA ACQUISITION METHOD AND IMAGE DATA ACQUISITION DEVICE

BACKGROUND OF THE INVENTION

1. Field of the Invention

The present invention relates to a photographed (radiographed) image data acquisition method and a photographed (radiographed) image data acquisition device which are applied to so-called CT (Computerized Tomography), which involves such operations as projecting cone-shaped radiation toward the subject from different directions of projection to acquire projected image data for each of the directions of projection, and on these projected image data, generating volume data for the subject.

2. Description of the Prior Art

Nowadays, in the field of medical video engineering, there is extensive research into technology for detecting three-dimensional radiation image information, and for example, the helical CT and the cone-beam CT have been proposed ("Cone-Beam CT—Present Status and Future Prospects" Image Information (M); January, 1988, p122 to p127. Refer to Japanese Unexamined Patent Publication No. 9 (1997)-253079).

Here, the "cone-beam CT" is the technology with which a radiation source and a two-dimensional radiation detector are disposed so that the subject is interposed between them; the radiation source and the radiation detector are turned around the subject relative to the subject while cone-shaped radiation is projected toward the subject from the radiation source; on the basis of the permeated radiation image data (precisely speaking, the projected image data) for the subject in the different angular positions, i.e., for the directions of projection which is obtained by detecting, with the radiation detector, the radiation which permeates the subject, the volume data for the subject is acquired; on the basis of the volume data, a three-dimensional image or a tomographic image is displayed on an image display device, or a three-dimensional image or the like is once stored in a memory device. Here, "the radiation detector" refers to a detector mainly consisting of a semiconductor which detects the radiation, and converts it into an electric signal.

Incidentally, with the above-stated conventional cone-beam CT, the region where a three-dimensional image or a tomographic image can be displayed is limited to within the inscribed circle for the region provided by the overlapping portion for all the directions of projection, specifically, for the projection region for all the radiant rays which is formed by the cone-shaped radiation in each direction of projection, when the radiation detector has an area large enough to detect all the cone-shaped radiant rays. Therefore, the region where an image can be displayed is determined by the projection angle for the radiation and the detection region for the radiation detector, and if the image region is to be enlarged, it is required to project a wider angle of cone-shaped radiation (hereafter called "wide-angle radiation") on the subject, and, with the detector, to detect the wide-angle radiation which permeates the subject. In other words, it is required to use a large-area detector, and project radiation having a projecting angle wide enough to cover the entire surface of the detector.

However, it is difficult to manufacture a large-area radiation detector having a large detection region, and if it could be manufactured, the manufacturing cost would be high, resulting in an expensive device. Therefore, with the conventional CT, it has been difficult to display an image of a large region.

The first photographed image data acquisition method according to the present invention is a photographed image data acquisition method with which a radiation source and a radiation detector disposed so that the subject is interposed between them are turned around the subject relative to the subject while cone-shaped radiation is projected toward the subject from the radiation source, and the radiation which permeates the subject is detected with the radiation detector to obtain photographed image data for the subject, in which the entire detection region for each of the direction of projections is divided into a plurality of partial regions; the partial radiation detector is moved to each of these partial regions formed by the division; and by synthesizing the photographed image data for the partial regions which is obtained by detecting, with the partial radiation detector, the radiation which permeates the subject for each of the partial regions, the photographed image data for the entire detection region is obtained.

Here, "photographed image data for the subject" means permeated radiation image data and projected image data or volume data, further, image data for output which carries a projected image, a three-dimensional image, or a tomographic image. Here, "output" means outputting of image data to an image display device, a printing device, a memory device, or other device which can input image data. These definitions are also applicable hereinbelow.

"By synthesizing the photographed image data for the partial regions, the photographed image data for the entire detection region is obtained" refers to any processing which synthesizes the permeated radiation image data or the like for the partial regions to obtain the permeated radiation image data or the like for the entire detection region. For example, it refers to obtaining volume data for the entire detection region on the basis of the projected image data for the partial regions, obtaining image data for output carrying a tomographic image for the entire detection region on the basis of the volume data for the partial regions, or the like, as well as synthesizing the permeated radiation image data for the partial regions to obtain the permeated radiation image data for the entire detection region, synthesizing the projected image data for the partial regions to obtain the projected image data for the entire detection region or synthesizing the volume data for the partial regions to obtain the volume data for the entire detection region.

In moving the partial radiation detector to each of the partial regions formed by the division, it is moved so that each of the partial regions formed by the division is completely covered by the detection region, in other words, the detection region covers each of the partial regions. In this way, for each of the directions of projection, the partial radiation detector is moved in increments of the specified distance corresponding to the above-mentioned division, and in each of the changed-over photographing positions, the photographed image data for the partial regions which is obtained by detecting, with the partial radiation detector, the radiation which permeates the subject is synthesized to obtain the photographed image data for the entire detection region. The number of partial radiation detectors may be one or more than one.

With this first photographed image data acquiring method, it is, of course, preferable to make the above-mentioned division so that the plurality of partial regions are consecutive. In other words, it is preferable that the above-mentioned specified distance in increments of which the partial radiation detector is to be moved be such that the adjacent detection regions for the radiation detector in each of the photographing positions overlap each other.

The second photographed image data acquiring method according to the present invention is a photographed image data acquiring method with which a radiation source and a radiation detector disposed so that the subject is interposed between them are turned around the subject relative to the subject while cone-shaped radiation is projected toward the subject from the radiation source, and the radiation which permeates the subject is detected with the radiation detector to obtain photographed image data for the subject, in which a plurality of partial radiation detectors disposed in such an arrangement that the entire detection region is covered constitute the radiation detector; and by synthesizing the photographed image data which is obtained by detecting, with the plurality of partial radiation detectors, the radiation which permeates the subject, the photographed image data for the entire detection region is obtained.

Here, "By synthesizing the photographed image data which is obtained by detecting, with the plurality of partial radiation detectors, the radiation which permeates the subject, the photographed image data for the entire detection region is obtained" refers to any processing which synthesizes the permeated radiation image data or the like obtained by detecting, with the plurality of partial radiation detectors, the radiation which permeates the subject to obtain the permeated radiation image data or the like for the entire detection region. For example, it refers to obtaining volume data for the entire detection region on the basis of the projected image data, obtaining image data for output carrying a tomographic image for the entire detection region on the basis of the volume data for the partial regions, or the like, as well as synthesizing the permeated radiation image data to obtain the permeated radiation image data for the entire detection region, synthesizing the projected image data to obtain the projected image data for the entire detection region or synthesizing the volume data to obtain the volume data for the entire detection region.

With this second photographed image data acquiring method, it is preferable to dispose the plurality of partial radiation detectors so that the adjacent detection regions overlap each other.

The first photographed image data acquiring device according to the present invention is a photographed image data acquiring device which realizes the above-stated first photographed image data acquiring method, i.e., a photographed image data acquiring device which is equipped with a radiation source and a radiation detector disposed so that the subject is interposed between them; and turns the radiation source and the radiation detector around the subject relative to the subject while projecting cone-shaped radiation toward the subject from the radiation source, detecting the radiation which permeates the subject with the radiation detector to obtain photographed image data for the subject, comprising:

a partial radiation detector;

mover means which moves the partial radiation detector to each of a plurality of partial regions formed by dividing the entire detection region for each of the directions of projection; and photographed image data synthesizer means which, by synthesizing the photographed image data for the partial regions obtained by detecting, with the partial radiation detector, the radiation that permeates the subject for each of the partial regions to which the partial radiation detector is moved, provides the photographed image data for the entire detection region.

In moving the radiation detector to each of the partial regions formed by the division, it is preferable to move the radiation detector so that each of the partial regions formed by the division is covered by the detection region. In other words, it is preferable that the above-mentioned moving means move the partial radiation detector in increments of the specified distance corresponding to the above-mentioned division for each of the directions of projection. Further, it is preferable that the division be made so that the plurality of partial regions are consecutive, in other words, the above-mentioned movement is made in increments of the distance which causes the adjacent detection regions for the partial radiation detector to overlap each other in each of the photographing positions.

The second photographed image data acquiring device according to the present invention is a photographed image data acquiring device which realizes the above-stated second photographed image data acquiring method, i.e., a photographed image data acquiring device which is equipped with a radiation source and a radiation detector disposed so that the subject is interposed between them; and turns the radiation source and the radiation detector around the subject relative to the subject while projecting cone-shaped radiation toward the subject from the radiation source, detecting the radiation which permeates the subject with the radiation detector to obtain photographed image data for the subject, in which the radiation detector comprises a plurality of partial radiation detectors disposed in such an arrangement that the entire detection region is covered; and comprising photographed image data synthesizer means which, by synthesizing the photographed image data obtained by detecting, with each of the plurality of partial radiation detectors, the radiation that permeates the subject, provides the photographed image data for the entire detection region.

It is preferable that the plurality of partial radiation detectors for this second photographed image data acquiring device be disposed so that the adjacent detection regions overlap each other.

With the first photographed image data acquiring method and the first photographed image data acquiring device according to the present invention, the entire detection region for each of the directions of projection is divided into a plurality of partial regions; the partial radiation detector is moved to each of these partial regions formed by the division; and by synthesizing the photographed image data for the partial regions which is obtained by detecting, with the partial radiation detector, the radiation that permeates the subject for each of the partial regions to which the partial radiation detector is moved, the photographed image data for the entire detection region is obtained. Therefore, on the basis of the permeated radiation image data or the projected image data for the entire detection region which is synthesized, the volume data for the entire detection region can be generated or the volume data for the entire detection region can be synthesized, and thus, without using a large-area radiation detector, a three-dimensional image or a tomographic image of a region larger than the photographing capable region which is defined by the detection region for the small-area detector can be formed for display output or other purpose. If the division is made so that the plurality of partial regions are consecutive, no regions where the acquired photographing image data is not detected are produced, and thus a smooth image having no seams can be obtained.

On the other hand, with the second photographed image data acquiring method and the second photographed image data acquiring device according to the present invention, the radiation detector is constituted by a plurality of partial radiation detectors disposed in such an arrangement that the entire detection region is covered, and by synthesizing the photographed image data obtained by detecting, with each of the plurality of partial radiation detectors, the radiation that permeates the subject, the photographed image data for the entire detection region is obtained. Therefore, as is the case with the first photographed image data acquiring method and the first photographed image data acquiring device, on the basis of the permeated radiation image data or the projected image data for the entire detection region which is synthesized, the volume data for the entire detection region can be generated or the volume data for the entire detection region can be synthesized, and thus, without using a large-area radiation detector, a three-dimensional image or a tomographic image of a region larger than the photographing capable region which is defined by the detection region for the small-area detector can be formed for display output or other purpose.

If the plurality of partial radiation detectors are disposed so that the adjacent detection regions overlap each other, no regions where the acquired photographing image data is not detected are produced, and thus a smooth image having no seams can be obtained.

SUMMARY OF THE INVENTION

The purpose of the present invention is to offer a photographed image data acquiring method and a photographed image data acquiring device for cone-beam CT which is capable of providing such a function as displaying an image of a region larger than the photographing capable region defined by the detection region without using a large-area radiation detector.

DESCRIPTION OF THE PREFERRED EMBODIMENTS

Figure 1:
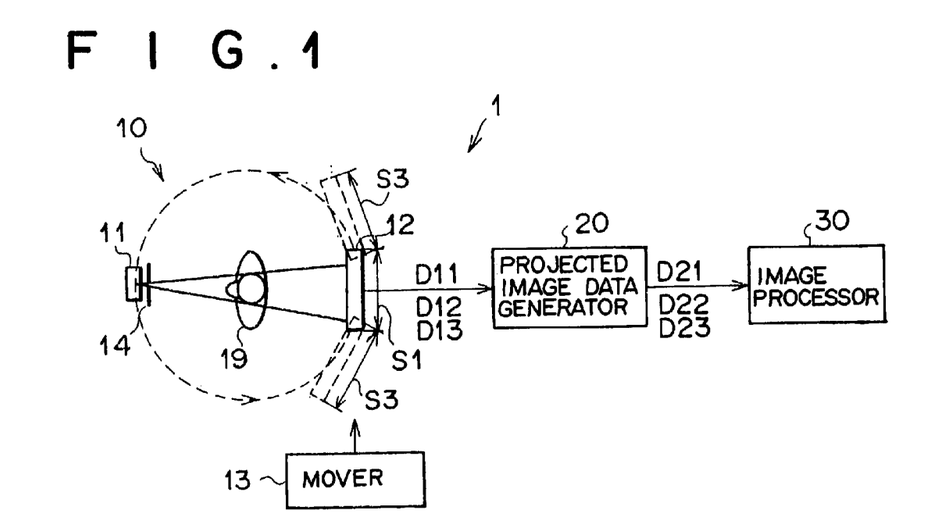
FIG. 1 is a block diagram illustrating the configuration of a cone-beam CT having one radiation detector to which a photographed image data acquiring device according to an embodiment of the present invention is applied.
Figure 2A:
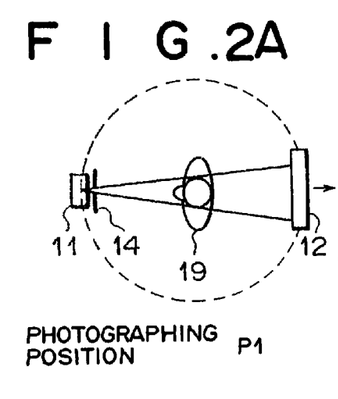
FIG. 2A, FIG. 2B, and FIG. 2C are drawings illustrating an entire detection region SO for a particular direction of projection, partial regions S1, S2, and S3, and photographing positions P1, P2, and P3 each corresponding to the respective partial regions.
Figure 2B:
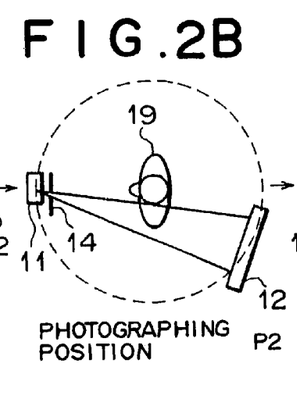
Figure 2C:
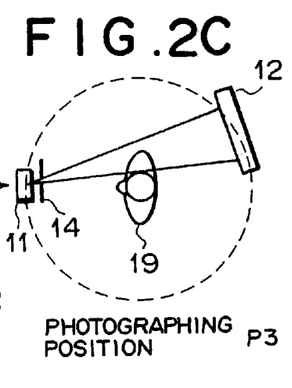

Hereinbelow, an embodiment of a photographed image data acquiring method and a photographed image data acquiring device according to the present invention will be explained in detail with reference to the drawings. FIG. 1 is a block diagram illustrating the schematic configuration of a cone-beam CT to which a photographed image data acquiring device according to an embodiment of the present invention is applied. FIG. 2A, FIG. 2B, and FIG. 2C show an entire detection region S0 for a particular direction of projection, partial regions S1, S2, and S3, which are consecutive divisions of it, and photographing positions P1, P2, and P3 each corresponding to the respective partial regions. Here, "the photographing position corresponding to a partial region" means the disposed position of the radiation detector to acquire the projected image data for that partial region (this definition is also applicable hereinbelow).

As shown in FIG. 1, this cone-beam CT1 comprises a photographing system 10 provided with a radiation source 11 and a two-dimensional radiation detector 12 as a partial radiation detector, mover means 13 to move the two-dimensional radiation detector 12, projected image data generator means 20, and an image processor section 30. To the image processor section 30 are connected image memory means (not shown) to store a variety of image data, and image display means (not shown) to display-output a 3-D image or a tomographic image as a visible image which is formed by the image processor section 30. Here, "a 3-D image" means a three-dimensional image which is visually three-dimensionally observed (a three-dimensional image and an image which is visually three-dimensionally observed although it is two-dimensional image).

This cone-beam CT1 also comprises rotation controller means (not shown) which turns the radiation source 11 and the two-dimensional radiation detector 12 around the subject 19 relative to the subject 19. This rotation controller means may be of any type, as long as it can sequentially change over the direction of radiation projection over the entire perimeter of the subject 19. For example, it may be of photographing system rotation type, which turns the radiation source 11 and the detector 12 around the subject 19, or of subject rotation type, which turns the subject 19 about the center line of the subject 19.

Mover means 13 is means to move the radiation detector 12 in accordance with the later described procedure to each of the partial regions S1, S2, and S3 formed by dividing the entire detection region S0 for each of the directions of projection, by which the radiation that permeates the subject 19 is detected by the detector 12 in each of the changed-over photographing positions. In other words, the detector 12 is moved in increments of the specified distance corresponding to the division for each of the directions of projection, and in each of the changed-over photographing positions, detects the radiation which permeates the subject 19. For the direction of projection as shown in FIG. 2, the photographing positions are named P1, P2, and P3 so that these correspond to the respective partial regions S1, S2, and S3. Needless to say, the composed region of the detection regions for the radiation detector 12 in these P1, P2, and P3 is approximately equal to the entire detection region S0 for this direction of projection. Even when the direction of projection is changed over by turning the radiation source 11 and the radiation detector 12 around the subject 19 relative to the subject 19, the relationship among the photographing positions P1, P2, and P3 is kept unchanged. The number of partial regions formed by dividing the entire detection region, in other words, the number of photographing positions may be varied for each of the directions of projection.

To prevent radiation not contributing to the detection from being projected onto the subject 19, the photographing system 10 is provided with a slit 14 which controls the direction of projection of the radiation in synchronization of the changeover of the photographing position. Needless to say, the slit 14 is turned around the subject 19 relative to the subject 19 in synchronization of the changeover of the direction of projection.

As projected image data generator means 20, the projected image data generator which is used with the conventional cone-beam CT can be used.

The image processor section 30 provides projected image data (a style of photographed image data) D20 for the entire detection region S0 by synthesizing the projected image data D21, D22, and D23 for the partial regions which are obtained by detecting, with the detector 12, the radiation which permeates the subject 19 for each of the partial regions to which the detector 12 is moved, i.e., in the photographing positions P1, P2, and P3. On the basis of the synthesized projected image data D20, volume data for the entire detection region S0 is generated, and on the basis of the volume data, image data for output which carries a 3-D image, a tomographic image, or the like is generated, the image data for output being outputted to such a device as an image display device (not shown). As the method for generating volume data, or generating image data for output which carries a 3-D image, a tomographic image, or the like, any method may be used. A specific example of a method will be given later.

Hereinbelow, the function of the cone-beam CT1 will be explained. First, the function of the mover means 13 will be explained.

First, as shown in FIG. 2, explanation will be given of an application where the radiation detector 12 is disposed in a particular photographing position, and with the photographing position relationship being held, the radiation source 11 and the radiation detector 12 are turned around the subject 19 relative to the subject 19, and this is repeated in the other photographing positions. Here, "the photographing position relationship" means the relative position relationship among the radiation source 11, the radiation detector 12, and the subject 19 with respect to the center of rotation of the cone-beam CT1.

The mover 13 first disposes the radiation detector 12 in the photographing position P1 where the detection region for the radiation detector 12 covers the partial region S1 (see FIG. 2A). Next, while cone-shaped radiation is being projected toward the subject 19 from the radiation source 11, the rotation controller means (not shown) turns the radiation source 11 and the radiation detector 12 around the subject 19 relative to the subject 19 with this photographing positioned relationship being held.

For each of the directions of projection in this turn (for each 30 degrees, for example), the radiation detector 12 detects the radiation which permeates the subject 19. The permeated radiation image data D11 thus detected for each of the directions of projection is inputted to the projected image data generator means 20. The projected image data generator means 20 provides a variety of signal processes, such as γ compensation and image distortion correction, for the permeated radiation image data D11 for each of the directions of projection, and generates projected image data D21 for each of the directions of projection for the subject 19 in this photographing position P1 to input it to the image processor section 30. The image processor section 30 temporarily stores the inputted projected image data D21 in the image memory means (not shown), relating it to the photographing position P1.

After completion of the processing in the photographing position P1, the mover means 13 moves the radiation detector 12 to the photographing position P2 where the detection region for the radiation detector 12 covers the partial region S2 (see FIG. 2B). In this photographing position P2, radiation is projected over the entire perimeter of the subject 19, and as is the case with the photographing position P1, projected image data D22 for each of the directions of projection is generated, and the projected image data D22 is stored in the image memory means, being related to the photographing position P2 at this time. After completion of the processing in the photographing position P2, processing is carried out in the same way for the photographing position P3 (see FIG. 2C). The projected image data in the photographing position P3 is denoted by D23.

In this way, the projected image data D21, D22, and D23 (hereafter expressed as D2 when collective expression of them is required) in the photographing positions for each of the directions of projection are acquired. The projected image data D2 acquired in the photographing positions is the projected image data for the entire detection region for a particular direction of projection, and the data D21, D22, and D23 are the projected image data for the respective partial regions formed by dividing the entire detection region.

Figure 3A:
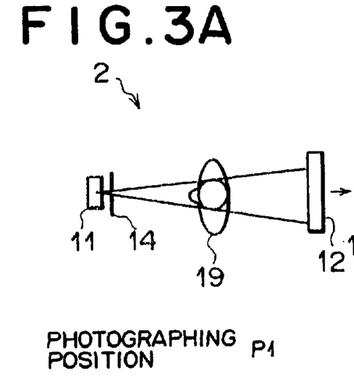
FIG. 3A, FIG. 3B, and FIG. 3C are drawings illustrating another method of moving the radiation detector.
Figure 3B:
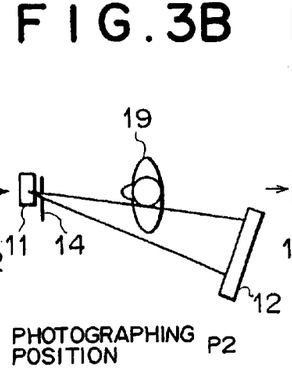
Figure 3C:
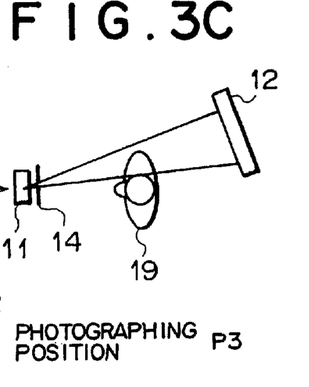

The method for acquiring the projected image data in the photographing positions for the directions of projection, i.e., the projected image data for the entire detection region for the directions of projection is not limited to the method stated above. For example, as shown in FIG. 3, first for a particular direction of projection, the radiation detector 12 is moved and disposed in each of the photographing positions. After acquiring the projected image data D2 in the photographing positions, the radiation source 11 and the radiation detector 12 are turned around the subject 19 relative to the subject 19 to change over the direction of projection. For this changed-over direction of projection, the radiation detector 12 is also moved and disposed in each of the photographing positions to acquire the projected image data D2, and such processing may be repeated.

Next, the method for forming a 3-D image or a tomographic image of the subject 19 will be explained.

Figure 4:
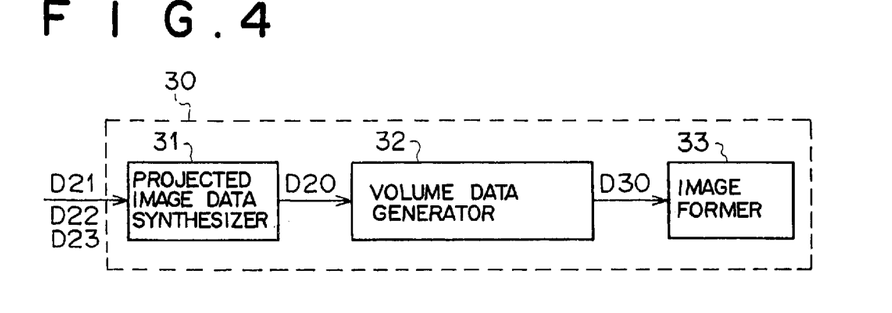
FIG. 4 is a circuit block diagram illustrating the detail of an image processor section.

FIG. 4 is a circuit block diagram illustrating the detail of a style of image processor section 30. As shown in FIG. 4, this image processor section 30 comprises projected image data synthesizer means 31 as photographed image data synthesizer means, volume data generator means 32, and image former means 33. The projected image data synthesizer means 31 synthesizes the projected image data D21, D22, and D23 for the entire detection region inputted from the projected image data generator means 20 for each of the directions of projection to provide synthesized projected image data D20 as one piece which covers the entire detection region.

As the method for providing this synthesized projected image data D20, any method may be used as long as the projected image data D21, D22, and D23 in the respective photographing positions can be used to provide synthesized projected image data D20 for an image region broader than the image region for the projected image data D2. In generating data for a connected region where detection regions overlap each other, it is preferable that image data which is connected smoothly in density gradient can be obtained.

Specific methods for providing this synthesized projected image data D20 include the method which sums up the projected image data D2 for each of the pixels and averages the sum. By this summing and averaging method, for the connected region where detection regions overlap each other, a plurality of projected image data included in the connected region are used to generate image data, and for the regions where no detection regions overlap each other, the image data for the respective regions are used as they are, which makes it possible to obtain synthesized projected image data D20 for an image region broader than the image region for the projected image data D2.

The volume data generator means 32 generates volume data on the basis of the synthesized projected image data D20 to provide synthesized volume data D30 which covers the entire detection region. The image former means 33 forms a 3-D image or a tomographic image on the basis of the synthesized volume data D30.

As the algorithm for generating volume data, the Feldkamp algorithm (Feldkamp L A, Davis L C, Kress J W, "Practical cone-beam algorithm", J. Opt. Soc. Am. A 1984;1:p612 to p619), the filter compensated reverse projection method (Handbook of Image Analysis (University of Tokyo Press), p356 to p371) and other well-known calculating methods for reconstruction of three-dimensional data are available. Detailed explanation of the method of generating volume data is omitted (also for the example given later).

Thus, if synthesized volume data is provided for each of the directions of projection on the basis of the synthesized projected image data as one piece which covers the entire detection region, and a 3-D image or a tomographic image is formed on the basis of the synthesized volume data, the synthesized volume data is practically equivalent to volume data which can be acquired by using a single large-area radiation detector which covers the entire detection region. Therefore, without using a large-area radiation detector, an image of a region larger than the photographing capable region which is defined by the detection region for the small-area detector can be formed for display output or other purpose.

In addition, the partial regions are provided as consecutive regions, and the detector is moved and disposed so that the detection region for the detector covers each of these partial regions. Therefore, no regions where projected image data is not detected are produced, and thus a smooth image having no seams can be obtained.

In addition, the projected image data for the partial regions can be acquired with the photographing positions being established on the same circumference so that the distance between the radiation source and the radiation detector is kept constant. As a result, the error resulting from variation in distance between the radiation source and the detection point on the radiation detector, i.e., the error in accordance with the enlargement ratio is smaller than that when a single large-area radiation detector is used.

Figure 5:
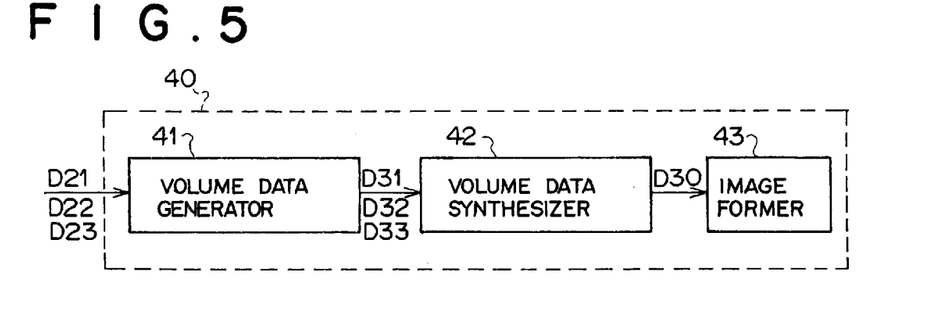
FIG. 5 is a circuit block diagram illustrating the detail of another image processor section.

FIG. 5 is a circuit block diagram illustrating another image processor section 40 which forms a 3-D image or a tomographic image of the subject 19. This image processor section 40 comprises volume data generator means 41, volume data synthesizer means 42 as photographed image data synthesizer means, and image former means 43. The volume data generator means 41 generates volume data D31, D32, and D33 in the respective photographing positions on the basis of the projected image data D21, D22, and D23. The volume data synthesizer means 42 synthesizes the volume data D31, D32, and D33 to provide synthesized volume data D30 as one block of data which covers the entire detection region. The image former means 43 forms a 3-D image or a tomographic image on the basis of the synthesized volume data D30.

As the method for providing synthesized volume data D30, any method may be used if the volume data D31, D32, and D33 in the respective photographing positions can be used to provide synthesized volume data D30 for an image region broader than the image region for the volume data, and the above-stated summing and averaging method may be used.

Thus, if synthesized volume data as one block of data which covers the entire detection region is provided for each of the directions of projection, and a 3-D image or a tomographic image is formed on the basis of the synthesized volume data, an image of a region larger than the photographing capable region which is defined by the detection region for the small-area detector can be formed without using a large-area radiation detector, as is the case with the image processor section 30 as shown in FIG. 4.

Figure 6:
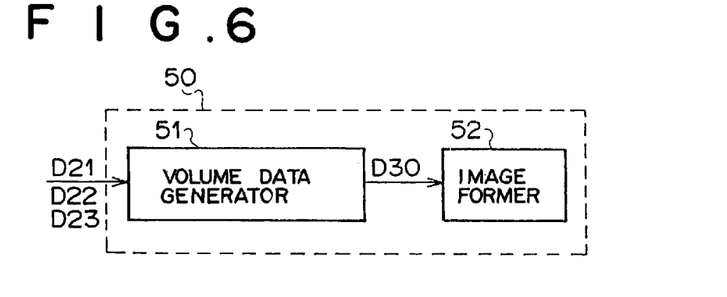
FIG. 6 is a circuit block diagram illustrating the detail of another image processor section.

FIG. 6 is a circuit block diagram illustrating another image processor section 50. The image processor section 50 comprises volume data generator means 51 as photographed image data synthesizer means, and image former means 52. The volume data generator means 51 uses, for a connected region for each of the directions of projection, a plurality of (preferably all) projected image data included in the connected region to generate volume data, thereby immediately providing, in the volume data generation process, synthesized volume data D30 as one block which covers the entire detection region. The image former means 52 forms a 3-D image or a tomographic image on the basis of the synthesized volume data D30.

Thus, if synthesized volume data is immediately provided in the volume data generation process, and a 3-D image or a tomographic image is formed on the basis of the synthesized volume data, an image of a region larger than the photographing capable region which is defined by the detection region for the small-area detector can be formed without using a large-area radiation detector, as is the case with the image processor section 30, 40.

Figure 7:
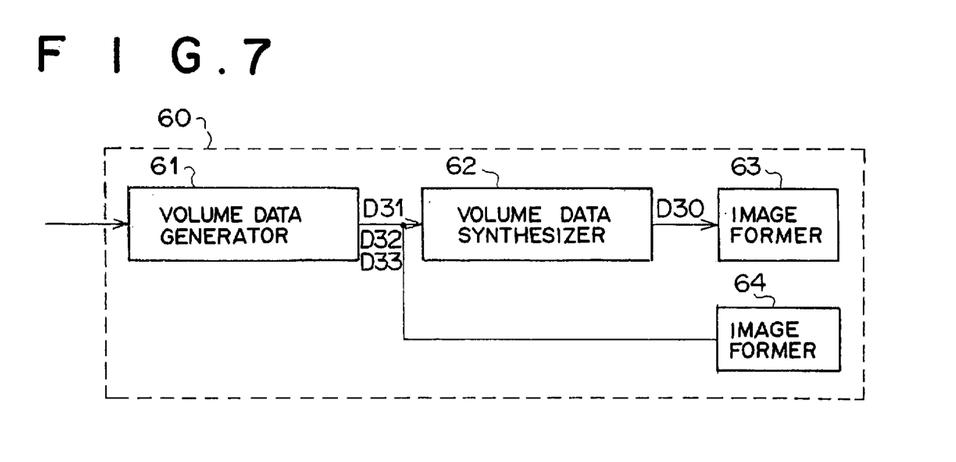
FIG. 7 is a circuit block diagram illustrating the detail of another image processor section.

FIG. 7 is a circuit block diagram illustrating another image processor section 60.

This image processor section 60 comprises volume data generator means 61, volume data synthesizer means 62, image former means 63, and image former means 64 as photographed image data synthesizer means. It is different from the image processor section 40 as shown in FIG. 5 in that the image former means 64 is further provided.

The volume data generator means 61 functions in the same way as the volume data generator means 41, and the volume data synthesizer means 62 functions in the same way as the volume data synthesizer means 42. The image former means 63 provides only the function of forming a 3-D image of the functions of the image former means 43. The image former means 64 forms a tomographic image in each of the photographing positions, i.e., for each of the partial regions on the basis of the volume data D31, D32, and D33 in the respective photographing positions, and then by synthesizing these, forms a synthesized tomographic image as one block which covers the entire detection region.

Thus, if a synthesized tomographic image as one block which covers the entire detection region is formed after forming a tomographic image in each of the photographing positions, a tomographic image of a region larger than the photographing capable region which is defined by the detection region for the small-area detector can be formed without using a large-area radiation detector, as is the case with the image processor section 30.

Incidentally, between the projected image data in one photographing position and that in another photographing position which are acquired as stated above, there is a discrepancy in time of photographing. As a result, a discrepancy in posture resulting from the respiration and the movement of the body during the interval between the shots is caused. Therefore, if the above-stated processing is carried out on the basis of the projected image data as acquired, a problem of a three-dimensional discrepancy in posture arises in the connected region for the synthesized image, and thus a smoothly connected image is not provided.

To solve this problem, it is preferable that at least for the connected region, registration or image distortion compensation be carried out using the correlation or the like for the image data (including the volume data) for that region.

Figure 8A:
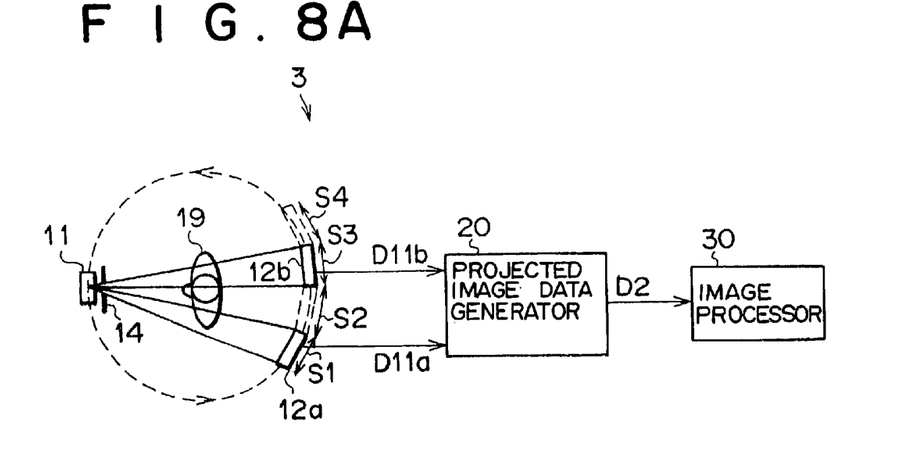
FIG. 8A is a block diagram illustrating the schematic configuration of a cone-beam CT having two radiation detectors.
Figure 8B:
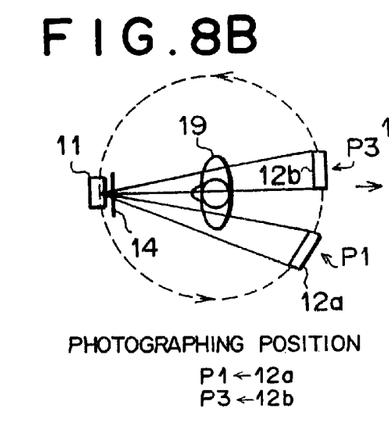
FIG. 8B and FIG. 8C are drawings illustrating an entire detection region SO for a particular direction of projection, partial regions S1, S2, S3, and S4, and photographing positions P1, P2, P3, and P4 corresponding to the respective partial regions.
Figure 8C:
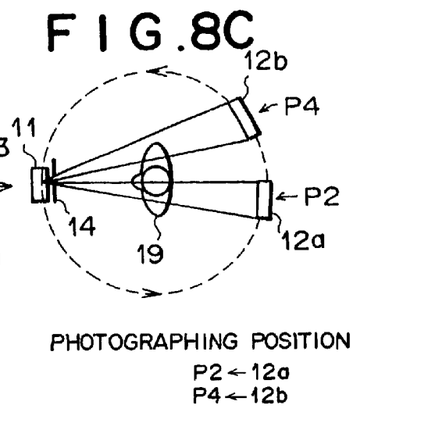

Next, a photographed image data acquiring method and a photographed image data acquiring device according to another embodiment will be explained. FIG. 8A is a block diagram illustrating the schematic configuration of a cone-beam CT2 to which this style of photographed image data acquiring device is applied, and FIG. 8B and FIG. 8C are drawings illustrating an entire detection region S0 for a particular direction of projection, partial regions S1, S2, S3, and S4 formed by dividing the region so, and photographing positions P1, P2, P3, and P4 corresponding to the respective partial regions. As shown in the figures, the cone-beam CT2 is different from the above-stated CT1 in that it has two radiation detectors 12a and 12b as the partial radiation detector.

With this cone-beam CT2, the entire detection region S0 for each of the directions of projection is divided into four consecutive partial regions S1, S2, S3, and S4 which are each narrower than the respective detection regions for the radiation detectors 12a and 12b. The radiation detectors 12a and 12b are moved by mover means (not shown) to each of the photographing positions in accordance with the specified procedure so that each of the partial regions formed by the division is covered by the detection region, and for each of the partial regions, i.e., in each of the photographing positions, the radiation which permeates the subject 19 is detected by the radiation detectors 12a and 12b. For the direction of projection as shown in FIG. 8A, FIG. 8B and FIG. 8C, the photographing positions are P1, P2, P3, and P4 where projected image data for the partial regions S1, S2, S3, and S4 can be acquired. If the detection regions for the radiation detectors 12a and 12b in these positions P1, P2, P3, and P4 are put together, a detection region approximately equal to the entire detection region for this direction of projection is provided. Even when the radiation source 11 and the radiation detectors 12a and 12b are turned around the subject 19 relative to the subject 19 to change over the direction of projection, the relationship among the photographing positions P1, P2, P3, and P4 is kept unchanged.

Next, the function of the cone-beam CT2 will be specifically explained. First, the radiation detector 12a is disposed in the photographing position P1 where the detection region for the radiation detector 12a covers the partial region S1, and the radiation detector 12b is disposed in the photographing position P3 where the detection region for the radiation detector 12b covers the partial region S3 (see FIG. 8B). Then, while cone-shaped radiation is being projected toward the subject 19 from the radiation source 11, the rotation controller means (not shown) turns the radiation source 11 and the radiation detectors 12a and 12b around the subject 19 relative to the subject 19 with this photographing position relationship being held.

For each of the directions of projection in this turn, the radiation detectors 12a and 12b detect the radiation which permeates the subject 19. The permeated radiation image data D11a thus detected by the radiation detector 12a for each of the directions of projection, and the permeated radiation image data D11b detected by the radiation detector 12b for each of the directions of projection are inputted to the projected image data generator means 20.

After completion of the processing in the photographing positions P1 and P3, the radiation detector 12a is moved and disposed in the photographing position P2 where the detection region for the radiation detector 12a covers the partial region S2, and the radiation detector 12b is moved and disposed in the photographing position P4 where the detection region for the radiation detector 12b covers the partial region S4 (see FIG. 8C). In these photographing positions P2 and P4, the radiation is projected over the entire perimeter of the subject 19, and as is the case with the photographing positions P1 and P3, the permeated radiation image data D11a and D11b for each of the directions of projection are inputted to the projected image data generator means 20.

The permeated radiation image data D11a and D11b are different from the permeated radiation image data D11 in the above-stated photographed image data acquiring device 1 in that they are acquired with different radiation detectors, respectively. However, in the variety of processes on the projected image data generator means 20 and in the image processor section 30 at the subsequent stages, the same processing as that with the above-stated device 1 can be carried out by relating the permeated radiation image data D11a and D11b to the respective photographing positions, and therefore, the processing will not affected by the number of radiation detectors to acquire image data. In other words, as long as the permeated radiation image data and the projected image data in the photographing positions can be acquired, which radiation detector it is detected by can be disregarded, and the number of detectors can also be disregarded. When a plurality of radiation detectors are used, and their characteristics are not uniform, it is, of course, preferable that the non-uniformity be compensated for so that equivalent data can be obtained.

In this way, with this embodiment, the projected image data in the photographing positions is acquired for each of the directions of projection. The projected image data acquired in the photographing positions is the projected image data for the entire detection region for a particular direction of projection, and the D21, D22, and D23 are the projected image data for the respective partial regions formed by dividing the entire detection region. In other words, also with this photographed image data acquiring device 2, if the same processing as with the above-stated photographed image data acquiring device 1 is carried out to form a 3-D image or a tomographic image, an image of a region larger than the detection region which is defined by the detection region for the radiation detector can be formed without using a large-area radiation detector.

Figure 9A:
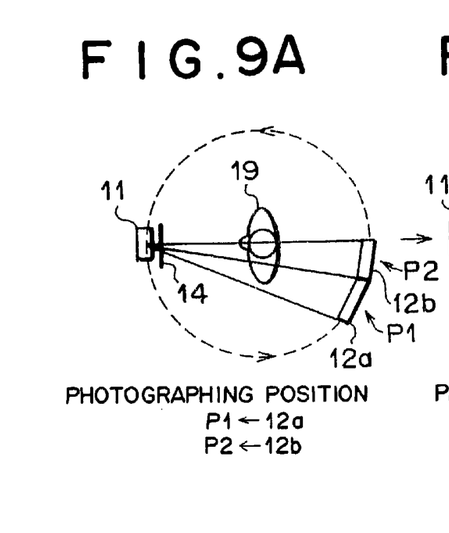
FIG. 9A, and FIG. 9B are drawings illustrating another method of moving the radiation detector of a cone-beam CT having two radiation detectors.
Figure 9B:
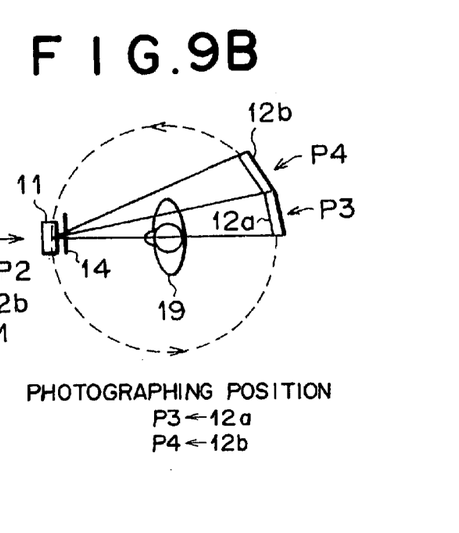

With the above-stated embodiment, after the radiation detector 12a has been disposed in the photographing position P1, and the radiation detector 12b has been disposed in the photographing position P3, the radiation detector 12a is moved and disposed in the photographing position P2, and the radiation detector 12b is moved and disposed in the photographing position P4. However, the way of changing over the photographing position is not always limited to this. For example, as shown in FIG. 9A and FIG. 9B, after the radiation detector 12a has been disposed in the photographing position P1, and the radiation detector 12b has been disposed in the photographing position P2, the radiation detector 12a and the radiation detector 12b may be moved and disposed in the photographing positions P3 and P4, respectively.

In addition, also with this photographed image data acquiring device 2, as is the case with the application as shown in FIG. 3, first for a particular direction of projection, the radiation detectors 12a and 12b are moved and disposed in each of the photographing positions. After acquiring the projected image data D2 in the photographing positions, the radiation source 11 and the radiation detectors 12a and 12b are turned around the subject 19 relative to the subject 19 to change over the direction of projection. For this changed-over direction of projection, the projected image data D2 is acquired in the same way as stated above, and such processing may be repeated. In other words, with the present invention, as long as the permeated radiation image data and the projected image data in the photographing positions can be acquired, the number of radiation detectors can be disregarded, and the detectors may be moved in any way.

Figure 10A:
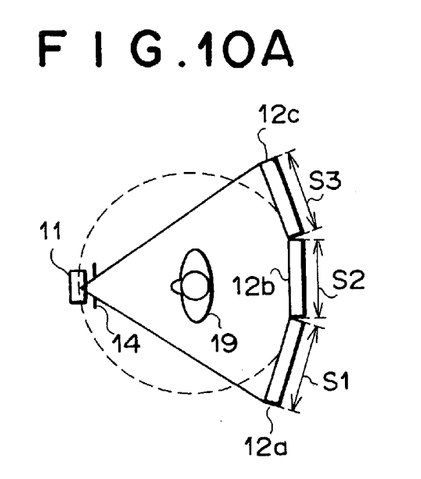
FIG. 10A and FIG. 10B are drawings illustrating three radiation detectors disposed so as to correspond to an entire detection region SO for a particular direction of projection and partial regions S1, S2, and S3, of a cone-beam CT having three radiation detectors.
Figure 10B:
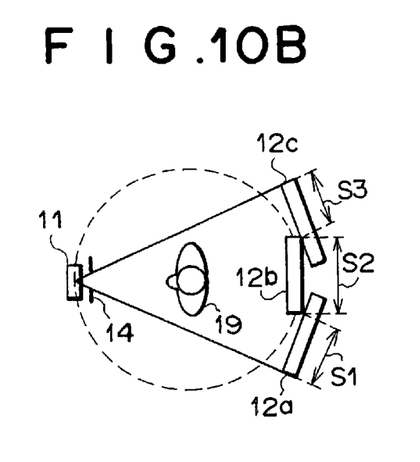

Next, a photographed image data acquiring method and a photographed image data acquiring device according to still another embodiment will be explained. FIG. 10A and FIG. 10B show, for a cone-beam CT3 to which this style of photographed image data acquiring device is applied, an entire detection region S0 for a particular direction of photographing, partial regions S1, S2, and S3 formed by dividing the region so, and photographing positions where the permeated radiation image data for the respective partial regions can be acquired, in other words, radiation detectors 12a, 12b, and 12c as three partial radiation detectors disposed in such an arrangement as to cover the entire detection region S0. With this embodiment, the three radiation detectors 12a, 12b, and 12c can be regarded as components which constitute a single radiation detector.

When a plurality of radiation detectors are used, and their characteristics are not uniform, it is, of course, preferable that the non-uniformity be compensated for so that equivalent data can be obtained.

Further, as shown in FIG. 10A, if the three radiation detectors 12a, 12b, and 12c are disposed so that they are simply adjacent to one another, regions where projected image data is not detected are produced because the edge portion of a detector provides a region where projected image data cannot be detected. Then, as shown in FIG. 10B, if the radiation detectors are disposed so that the adjacent detection regions overlap each other, no regions where projected image data is not detected are produced, and thus a smooth image having no seams can be obtained.

With this cone-beam CT3, for a particular direction of projection, the radiation which permeates the subject 19 is detected with the three radiation detectors 12a, 12b, and 12c disposed in the respective photographing positions. The projected image data for the entire detection region for that direction of projection is acquired, and after that the radiation source 11 and the radiation detectors 12a, 12b, and 12c are turned around the subject 19 relative to the subject 19 to change over the direction of projection. For this changed-over direction of projection, the projected image data is acquired in the same way as stated above, and such processing is repeated. In this way, the projected image data for the entire detection region for each of the directions of projection can be acquired. The projected image data acquired is the projected image data for the partial regions formed by dividing the entire detection region for a particular direction of projection. Therefore, also with this photographed image data acquiring device 3, if the same processing as that with the above-stated photographed image data acquiring device 1 is made to form a 3-D image or a tomographic image, an image of a region larger than the detection region which is defined by the detection region for the small-area radiation detector can be formed without using a large-area radiation detector.

Thus, the photographed image data acquiring device according to the present invention may be any photographed image data acquiring device with which, by dividing the entire detection region and acquiring projected image data for the partial regions formed by the division, the projected image data for the entire detection region for each of the directions of projection is acquired. The number of detectors to acquire the projected image data for the partial regions can be disregarded, and whether the projected image data for the partial regions is acquired by moving the radiation detector or by providing detectors corresponding to the respective partial regions can also be disregarded.

The above explanations have all been given with respect to an embodiment with which the projected image data for the partial regions is temporarily generated, and then the synthesized projected image data or the synthesized volume data is generated. However, the present invention is not always limited to such an embodiment. In other words, the photographed image data acquiring device according to the present invention may be any photographed image data acquiring device with which, by dividing the entire detection region into a plurality of partial regions and, for the partial regions formed by the division, synthesizing the image data obtained by detecting the radiation which permeates the subject, the image data for the entire detection region is obtained. For example, by synthesizing the permeated radiation image data obtained by detecting the radiation which permeates the subject for the partial regions, the synthesized permeated radiation data may be obtained.

What is claimed is:

1. A photographed image data acquiring method in which a radiation source and a radiation detector disposed so that a subject is interposed between them are turned around said subject relative to the subject while cone-shaped radiation is projected toward said subject from said radiation source, and the radiation which permeates said subject is detected with said radiation detector to obtain photographed image data for said subject, said radiation detector comprising a partial radiation detector, wherein the entire detection region for each of the directions of projection is divided into a plurality of partial regions adjacent to each other; the partial radiation detector is moved to each of these partial regions formed by the division; and by synthesizing the photographed image data for the partial regions which is obtained by detecting, with said partial radiation detector, the radiation which permeates said subject, for each of the partial regions, said photographed image data for said entire detection region is obtained, wherein the partial radiation detector is operable to partially overlap adjacent partial regions during detection to obtain the photographed image data for said entire detection region.

2. The method of claim 1, wherein said radiation source is disposed in a housing which is maintained in a fixed position during radiation detection of the entire detection region.

3. A photographed image data acquiring method in which a radiation source and a radiation detector disposed so that a subject is interposed between them are turned around said subject relative to the subject while cone-shaped radiation is projected toward said subject from said radiation source, and the radiation which permeates said subject is detected with said radiation detector to obtain photographed image data for said subject, wherein said radiation detector comprises a plurality of partial radiation detectors disposed in such an arrangement that the entire detection region is covered; and by synthesizing the photographed image data which is obtained by detecting, with said plurality of partial radiation detectors, the radiation which permeates said subject, said photographed image data for said entire detection region is obtained, wherein said plurality of partial radiation detectors are disposed so that the adjacent detection regions overlap each other.

4. A photographed image data acquiring device which is equipped with a radiation source and a radiation detector disposed so that a subject is interposed between them, and turns said radiation source and said radiation detector around said subject relative to the subject while projecting cone-shaped radiation toward said subject from said radiation source, detecting the radiation which permeates said subject with said radiation detector to obtain photographed image data for said subject, comprising:

a partial radiation detector;

mover means which moves said partial radiation detector to each of a plurality of partial adjacent regions formed by dividing the entire detection region for each of the directions of projection, said mover means moving the partial radiation detector to partially overlap adjacent partial regions during detection; and photographed image data synthesizer means which, by synthesizing the photographed image data for the partial regions obtained by detecting, with said partial radiation detector, the radiation that permeates said subject for each of the partial regions to which said partial radiation detector is moved, provides said photographed image data for said entire detection region.

5. The device of claim 4, wherein said radiation source is disposed in a housing which is maintained in a fixed position during radiation detection of the entire detection region.

6. A photographed image data acquiring device which is equipped with a radiation source and a radiation detector disposed so that a subject is interposed between them; and turns said radiation source and said radiation detector around said subject relative to the subject while projecting cone-shaped radiation toward said subject from said radiation source, detecting the radiation which permeates said subject with said radiation detector to obtain photographed image data for said subject, wherein said radiation detector comprises a plurality of partial radiation detectors disposed in such an arrangement that the entire detection region is covered; and is provided photographed image data synthesizer means which, by synthesizing the photographed image data obtained by detecting, with each of said plurality of partial radiation detectors, the radiation that permeates said subject, provides said photographed image data for said entire detection region, wherein said plurality of partial radiation detectors are disposed so that the adjacent detection regions overlap each other.

7. A photographed image data acquiring device which is equipped with a radiation source and a radiation detector disposed so that a subject is interposed between them and turns said radiation source and said radiation detector around said subject relative to the subject while projecting cone-shaped radiation toward said subject from said radiation source, detecting the radiation which permeates said subject with said radiation detector to obtain photographed image data for said subject, wherein said radiation detector comprises a plurality of partial radiation detectors disposed in such an arrangement that the entire detection region is covered and the adjacent detection regions overlap each other; and is provided a photographed image data synthesizer which, by synthesizing the photographed image data obtained by detecting, with each of said plurality of partial radiation detectors, the radiation that permeates said subject, provides said photographed image data for said entire region.

* * * * *